United States Patent
Melby et al.

(10) Patent No.: US 6,365,140 B1
(45) Date of Patent: Apr. 2, 2002

(54) MODIFIED STARCH SOLUTIONS AND THEIR USE IN PERSONAL CARE

(75) Inventors: Allan L. Melby, Cranberry Township, PA (US); Manfred Gunther, Hamburg (DE); Tammy W. Gaffney, New Castle; Gary F. Matz, Carnegie, both of PA (US)

(73) Assignee: Calgon Corporation, Naperville, IL (US)

( * ) Notice: Subject to any disclaimer, the term of this patent is extended or adjusted under 35 U.S.C. 154(b) by 0 days.

(21) Appl. No.: 09/717,958

(22) Filed: Nov. 20, 2000

Related U.S. Application Data

(60) Provisional application No. 60/168,939, filed on Dec. 3, 1999.

(51) Int. Cl.$^7$ ................................................ A61K 7/06
(52) U.S. Cl. ..................... 424/70.1; 424/70.28; 424/65; 424/78.17; 127/32
(58) Field of Search ............................... 424/78.17, 65, 424/70.1, 70.28; 127/32

(56) References Cited

U.S. PATENT DOCUMENTS

| | | |
|---|---|---|
| 3,472,840 A * | 10/1969 | Stone et al. ................. 260/231 |
| 3,553,191 A | 1/1971 | Parmerter et al. |
| 3,565,887 A | 2/1971 | Parmerter et al. |
| 4,080,310 A | 3/1978 | Ng et al. |
| 4,205,063 A | 5/1980 | Khalil et al. |
| 4,292,212 A | 9/1981 | Melby |
| 4,676,978 A | 6/1987 | Cseh |
| 4,786,494 A | 11/1988 | Hirota et al. |
| 4,803,071 A | 2/1989 | Iovine et al. |
| 5,288,484 A | 2/1994 | Tashjian |
| 5,482,704 A | 1/1996 | Sweger et al. |
| 5,580,553 A * | 12/1996 | Nakajima ................. 424/78.17 |
| 5,776,476 A | 7/1998 | Billmers et al. |

FOREIGN PATENT DOCUMENTS

| | | |
|---|---|---|
| EP | 0308189 B1 | 3/1989 |
| EP | 0308190 B1 | 3/1989 |
| WO | WO 99/21532 A1 | 5/1999 |

OTHER PUBLICATIONS

Principles of Polymer Science and Technology in Cosmetics and Personal Care, ©1999 by Marcel Dekker, Inc. Chapter 8 by James V. Gruber, "Polysaccharide–Based Polymers in Cosmetics," pp. 325–389.

\* cited by examiner

Primary Examiner—Michael G. Hartley
Assistant Examiner—Michael A. Willis
(74) Attorney, Agent, or Firm—Margaret M. Brumm; Thomas M. Breininger

(57) ABSTRACT

Disclosed are novel aqueous modified starch solutions, such solutions can contain high levels of the modified starch and remain stable such that on standing, the solution does not form a precipitate, become a non pourable gel, separate or spoil due to attack from microorganisms. The use of the novel aqueous modified starch solutions in a cosmetically acceptable medium for the treatment of a keratin-containing substrate is also disclosed.

18 Claims, No Drawings

MODIFIED STARCH SOLUTIONS AND THEIR USE IN PERSONAL CARE

CROSS-REFERENCE TO RELATED PATENT APPLICATION

This patent application is claiming priority from Provisional U.S. Patent Application No. 60/168,939, filed Dec. 3, 1999, entitled, "MODIFIED STARCH SOLUTIONS AND THEIR USE IN PERSONAL CARE".

FIELD OF THE INVENTION

The present invention relates to novel aqueous solutions of modified starches, modified starch compositions and methods for using such modified starches and modified starch compositions in personal care applications. In general terms, the modified starches and modified starch compositions of the present invention are believed to be useful in the treatment of keratin-containing substrates. Keratin substrates include, but are not limited to, animal and human hair, skin and nails.

BACKGROUND OF THE INVENTION

The surface properties of keratin are of interest in cosmetic science, and there has been a long-standing desire to discover ingredients which will beneficially affect the topical and bulk condition of keratinous substrates, such as hair. For example, such ingredients must have adequate adherent properties, so that they are not only adsorbed initially, but are also retained on exposure to water. This property is referred to as "substantivity", i.e., the ability of a material to be adsorbed onto keratin and to resist removal by water rinse-off.

Hair is composed of keratin, a sulfur-containing fibrous protein. The isoelectric point of keratin, and more specifically of hair, is generally in the pH range of 3.2–4.0. Therefore, at the pH of a typical shampoo, about pH 5.4 to about pH 6.9, hair carries a net negative charge. Consequently, cationic polymers have long been used as conditioners in shampoo formulations, or as a separate treatment, in order to improve the wet and dry combability of the hair. The substantivity of the cationic polymers for negatively charged hair along with film formation provides for easier detangling during wet hair combing less static flyaway during dry hair combing. Cationic polymers generally also impart softness and suppleness to hair.

When cationic polymers are added to shampoos (or to skin care products such as cleaning compositions) containing anionic surfactants, formation of highly surface active association complexes generally takes place, which imparts improved foam stability to the shampoo. Maximum surface activity and foam stability, or lather, are achieved at near stoichiometric ratios of anionic surfactant: cationic polymer, where the complex is least water soluble. Generally, cationic conditioners exhibit some incompatibility at these ratios. Compatibility gives a commercially more desirable clear formulation, while incompatibility leads to a haze or precipitation, which is aesthetically less desirable in some formulations.

Hair fixative properties such as curl retention are believed to be directly related to film forming properties of cationic polymers, as well as to molecular weight, with performance generally increasing with increasing molecular weights However, the fixative properties conferred by cationic polymers generally tend to have a reciprocal relationship to other conditioning properties, i.e., good curl retention usually means that properties such as wet combability will suffer, and vice versa.

Aside from hair care uses, skin and nail conditioning products are desired which function to improve properties such as retention of moisture, softening of the skin, attraction of air moisture, retardation of water loss, feel and reduction of skin irritations caused by contact with cosmetic ingredients. Examples of such products include detergents, lotions and soaps.

Generally, two broad areas of skin care products have been recognized as skin conditioners: emollients and humectants. Emollients generally provide improved moisture retention in the skin and plasticization/softening of the skin. Common commercial emollients are mineral oil; petrolatum; aliphatic alcohols, such as stearyl alcohol; lanolin and its derivatives; glycol stearate; and fatty acids, such as triethanolamine oleate. Humectants generally attract moisture, retard evaporation of water from the skin surface, and plasticize/soften skin. Common commercial humectants include glycerin, propylene glycol, sorbitols, and polyethylene glycols.

A desirable skin conditioner should impart at least some of the attributes of an emollient or a humectant, as well as provide improved lubricity and feel to the skin after treatment and/or reduce skin irritation caused by other components in the conditioner such as, for example, soaps, detergents, foam boosters, surfactants, and perfumes. It is known by those skilled in the art that cationic polymers can be employed as skin and nail conditioners.

The skin and nail conditioning properties of lubricity, moisturizing and feel, are related to the film forming properties of the cationic polymers, as well as to molecular weight, with performance generally increasing with increasing molecular weight.

Synthetic cationic polymers have been used in cosmetic formulations for many years to achieve the properties described above. While these materials have many advantages as far as ease of handling and the ability to easily modify polymer compositions to achieve desired performance objectives, once they are used in a formulation by the consumer, they remain in the environment and do not readily decompose with time.

As concerns about environmental pollution and concentration of synthetic materials in public waterways have increased, it has become increasingly desirable to use materials that are derived from renewable resources and are inherently biodegradable after the personal care product is consumed.

Cationic derivatives of cellulose, guar and various proteins have been developed as naturally derived cationic polymers to be used as described above. These materials are supplied as dry powders and have demonstrated the ability to provide conditioning benefits to keratin based substrates. Handling these materials is generally difficult, however, as they must be dissolved into water as part of the formulating process. Problems arise if the dry material is added to quickly, the pH is wrong or insufficient mixing is used which results in "fish eyes" (insoluble particles), lumping or degradation of the polymer. These conditions can lead to a product with inadequate conditioning properties and non reproducibly performing final product formulations.

Keratin conditioning additives generally are of three primary types: cationic polymers, proteins or protein derivatives, and fatty quaternary ammonium compounds. Commonly used cationic polymers include: quaternary nitrogen-containing hydroxyethyl cellulose compounds, copolymers of vinylpyrrolidone and dimethylaminoethylmethacrylate, and amino functional polydimethylsiloxane. Hydrolyzed animal protein has been frequently used as a keratin conditioner. Also used are natural products such as collagen and casein. Suitable quaternary ammonium compounds include such products as distearyl dimethyl ammonium chloride.

Conditioning additives comprising copolymers of dimethyldiallylammonium chloride and other monomers are well known; see, e.g., EP 308189 (with acrylamide) and EP 0 308 190 and U.S. Pat. No. 4,803,071 (with hydroxyethyl cellulose). The use of such polymers in cosmetics is also described in Sykes et al., *Drug Cosmet. Ind.*, 126(2), 62, 64, 66, 68, 136 (1980).

Hair care compositions comprising cationic cellulose are well known. For example hydroxypropyl trimethyl ammonium chloride ethers of cellulose have been used in conditioning compositions; see, e.g., U.S. Pat. No. 5,288,484 as well as shampoo compositions; see, e.g., U.S. Pat. No. 4,205,063. U.S. Pat. No. 4,803,071 discloses the use in hair care compositions of cationic cellulose made from grafting dimethyldiallylammonium chloride onto the cellulose backbone.

Hydroxypropyl trimethyl ammonium chloride ethers of guar are catatonically modified guar gums that have also been used extensively in hair care compositions. U.S. Pat. No. 4,292,212 describes the use of this material in a shampoo crème rinse while U.S. Pat. No. 4,676,978 describes the use of this material in a shampoo.

Nonionic cellulosic materials have also found use in hair care formulations. Examples include shampoo compositions which comprise a nonionic cellulose ether compound; see, e.g., U.S. Pat. No. 4,786,494, and a hair conditioning composition comprising hydroxyethyl cellulose.

Modified starch materials have been used to a limited extent to treat keratin based substrates. Cosmetic compositions containing hydrophobic starch derivatives are disclosed in U.S. Pat. No. 5,776,476. Amphoteric aminomulticarboxylate modified starch is disclosed for modifying the rheological properties of cosmetic compositions in U.S. Pat. No. 5,482,704. These materials are used as thickeners, and as such, can only be prepared at low active levels in aqueous solution (on the order of 5–10%). Above these levels they form a gel or non flowable complex. A common household example of the use of starch as a thickener would be the use of corn starch to thicken gravy.

U.S. Pat. No. 4,080,310 suggests the use of a cationic starch in an amphoteric conditioning shampoo. The particular cationic starch disclosed, "Cato starch ex National Starch and Chemical Corporation, U.S.A." is supplied as a dry powder and believed to fall under the general Chemical Abstract Index Name of 2-Hydroxy-3-(trimethylammonio) propyl ether, chloride. This material is widely used in the manufacture of paper as both a process aid and sizing aid but is not used commercially to treat keratin based substrates such as hair, skin or nails.

A more complete review of the use of polysaccharide-based materials in cosmetic formulations is given in *Principles of Polymer Science and Technology in Cosmetics and Personal Care*, Marcel Dekker, Inc., 1999, Chapter 8, pages 325 to 389 which is incorporated by reference in its entirety.

As noted previously, prior to the present invention many of the polysaccharide-based materials available for use in formulations used to treat hair and skin are supplied as solid powder materials. There are three primary reasons for supplying these materials in a dry powder form. 1.) A powder is fairly easy to manufacture, i.e. the powder is simply formed from the raw materials without the need to formulate a liquid. 2.) A dry powder has very little storage problems, whereas a liquid starch material is a prime growth medium for microorganisms. 3.) A dry powder does not have the high shipping costs associated with transporting the large volume of water (90–95%) needed to provide a pourable dilute liquid starch solution.

The dry powder form of these polysaccharide-based materials, however, causes difficulties for end use formulators, as great care is required to dissolve the dry material during the formulation process. Some of the problems that arise, as mentioned above, are "fish eyes", which are bits of polysaccharide-based material that have not completely solubilized, and over mixing which is done to prevent "fish eyes" but has the negative consequence of degrading the polysaccharide-based material. These difficulties outlined can result in final formulations that do not perform for their intended use.

Water-soluble synthetic polymers can be used and are often supplied as an aqueous solution and overcome many of the difficulties outlined above. However, as stated, it has become desirable, particularly in certain geographies to use materials that are inherently biodegradable, which synthetic polymers, in general, are not.

There remains a need for an inherently biodegradable conditioning additive for hair and skin, which can provide the performance expected from a conditioning additive as well as the ease of use found with synthetic materials. More specifically, there is a need that the conditioning additive be derived from renewable resources and be supplied as an easy to pour aqueous solution. It is also vital that this aqueous solution be stable, maintaining a uniform appearance and not gel, separate or have the active ingredient precipitate from solution. Lastly, the aqueous solution should not spoil or degrade due to attack from microbes such as molds, yeast or bacteria.

SUMMARY OF THE INVENTION

The instant invention comprises novel water-soluble modified starches, modified starch compositions, and methods for treating keratin based substrates.

The aqueous solution of a modified starch according to the present invention comprises:

(a) about 20% to about 98.599%, by weight water;

(b) about 1% to about 49.5%, by weight of a modified starch;

(c) about 0.2% to about 15%, by weight of urea;

(d) about 0.2% to about 10% by weight of an alpha hydroxy acid or the corresponding alpha hydroxy acid salt with sodium, ammonium, potassium and/or any substituted amine, such as diethanolamine, triethanolamine, and monoethanolamine;

(e) zero up to about 5% by weight of an aliphatic carboxylic acid from $C_2$ to $C_{36}$ in chain length acid or the corresponding carboxylic acid salt with sodium, ammonium and/or potassium;

(f) about 0.001% to about 0.5% by weight of a preservative; and (g) having a pH of from about 1 to 9 wherein the modified starch of (b) is of the general formula:

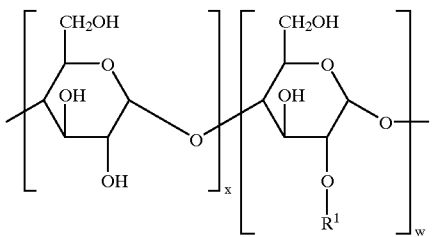

wherein $R^1$ is selected from the group consisting of ethers (1,2,3 and 4), ester (5) and amphoteric stubstituents (6, 7, 8 and 9) generally described as:

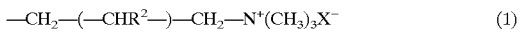  (1)

wherein m is an integer from 0 to 34, each $R^2$ can independently be H or OH, and $X^-$ is $Cl^-$ or $Br^-$;

  (2)

wherein m is as defined above and each $R^3$ can independently be H or OH;

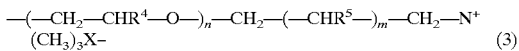  (3)

wherein n is an integer from 1 to 100, m is as defined above, each $R^4$ can independently be H, OH, $CH_3$ or $CH_2OH$, each $R^5$ can independently be H or OH, and $X^-$ is $Cl^-$ or $Br^-$;

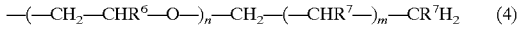  (4)

wherein n and m are as defined above, each $R^6$ can independently be H, OH, $CH_3$ or $CH_2OH$, each $R^7$ can independently be H or OH, and $X^-$ is $Cl^-$ or $Br^-$;

  (5)

wherein m is as defined above and each $R^8$ can independently be H, OH, $CH_3$ or $CH_2OH$;

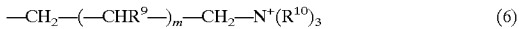  (6)

wherein m is as defined above, each $R^9$ can independently be H, OH, $CH_3$ or $CH_2OH$, and each $R^{10}$ can independently be:

(A) $-(CR^{11}H-)_p-CH_3$
(B) $-CH_2OH$
(C) $-(CR^{11}H-)_p-COOH$
(D) $-(CR^{11}H-)_p-COO^-$
(E) $-(CR^{11}H-)_p-SO_3^-$ wherein p is an integer from zero to 10 and each $R^{11}$ can independently be H, OH, $CH_3$ or $CH_2OH$;

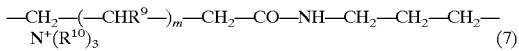  (7)

wherein m, $R^9$, and $R^{10}$ are as defined above;

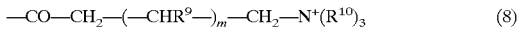  (8)

wherein m, $R^9$, and $R^{10}$ are as defined above;

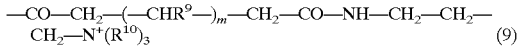  (9)

wherein m, $R^9$, and $R^{10}$ are as defined above;

wherein the mol % of substituted sugar units (w) out of the total sugar units along the starch molecule is between about 2 mol % to about 80 mol % and the mol % of unsubstituted sugar units (x) is between about 20 mol % to about 98 mol %.

Another aspect of the present invention also comprises a cosmetically acceptable medium containing an amount of the above aqueous solution of the modified starch. This amount of the aqueous solution of the modified starch is preferably about 0.01 to about 20%, based on the total weight of said medium.

A further aspect of the present invention entails a method for treating a keratin-containing substrate comprising contacting said substrate with an effective amount of the above defined aqueous solutions of modified starch conditioning additive, preferably with an effective amount of said additives or, an effective amount of a cosmetically acceptable medium comprising from about 0.01 to about 20%, preferably from about 0.1 to about 10%, by weight, based on the total weight of said medium, of an instant aqueous solution of modified starch conditioning additive.

DETAILED DESCRIPTION OF THE INVENTION

The inventors have unexpectedly discovered novel water-soluble modified starches and modified starch compositions for treating keratin. These water-soluble modified starches are in the form of a stable aqueous solution which is characterized by the fact that after standing at room temperature for six months the solution does not form a precipitate, become a non pourable gel or separate or spoil due to attack from microorganisms.

The inventors have also unexpectedly discovered novel water-soluble modified starches and modified starch compositions for treating keratin that are high in solids. The inventors have unexpectedly discovered that it is the high molecular weight and physical properties of currently available polysaccharide based materials that limit the active level (solids) that can be present in an aqueous solution. The inventors have discovered this absolute upper limit possible to be around 5 to 10% by weight. However, amounts actually used in the art are much less. Using levels in this range and above forms the solution into a gel or a non flowable complex. For this reason, prior to the present invention, aqueous solutions of modified polysaccharides (starch) have not been commercially available, or even viable, as the transportation costs and handling difficulties associated with the highly viscous or gelled dilute aqueous solutions made solutions very impractical.

The amount of modified starch present in the aqueous solution of the present invention is as low as about 1% by weight. However, when using preferred lower molecular weight modified starches this amount can be much higher, as high as about 50% by weight. The preferred amount of modified starch present in the aqueous solution of the present invention is above about 5%, preferably in the range of about 5% to about 40% by weight, more preferably about 10% to about 35%, with an amount of about 15% to about 35% being most preferred.

The modified starch present in the higher concentrated aqueous solution of the present invention preferably is of lower molecular weight. This molecular weight is preferably below about 10,000,000 weight average molecular weight, more preferably about 1,000 to about 1,000,000 with a weight average molecular weight of about 5,000 to about 500,000 being most preferred. The molecular weight is measured using gel permeation chromatography (GPC) which utilizes both refractive index (RI) and multiangle laser light scattering (MALLS) detectors.

Aqueous solutions of polysaccharides are also prone to phase separation and attack from microorganisms which leads to discoloration of the solution, degradation of the polysaccharide as well as odor. These problems are solved by the composition of the present invention. The inventors have unexpectedly discovered that urea prevents gellation and separation of the starch in solution. The inventors have also unexpectedly discovered that the use of an alpha hydroxy acid or the corresponding alpha hydroxy acid salt gellation and separation of the starch in solution. The inventors have further unexpectedly discovered preferred compatible preservatives or biocides that protect the composition from spoilage over time without any detriment to performance.

The present invention also relates to aqueous solutions of the aforesaid modified starch compositions which in addition to the modified starch contain stabilizers such as urea, lactic acid and/or other alpha carboxylic acids; and preservatives such as methyl paraben, propyl paraben, butyl paraben and sodium benzoate.

The modified starch of (b) according to the present invention is of the general formula:

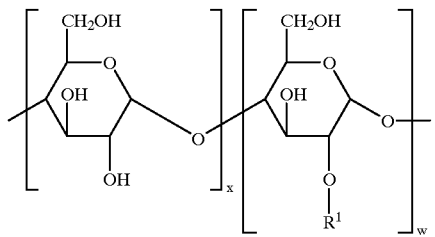

wherein $R^1$, x, and w are as defined above.

In particular, the instant invention is preferably directed to a cationic modified starch in which $R^1$ is (2) $-CH_2-(-CHR^2-)_m-CH_2-N^+(CH_3)_3X^-$, wherein m is an integer from 0 to 34, each $R^2$ can independently be H or OH, and $X^-$ is $Cl^-$ or $Br^-$. This starch is preferably of the general formula:

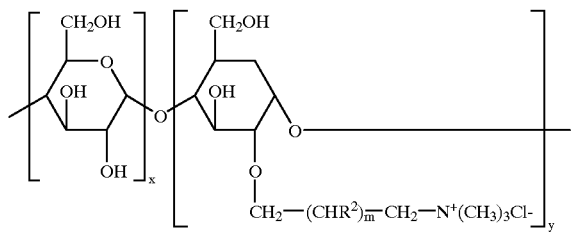

wherein where m is an integer from 0 to 34, $R^2$ can independently be H or OH, and the mol % of the cationic ether substituted sugar units (y) out of the total sugar units along the starch molecule comprises about 2 mol % to about 80 mol % and the mol % of unsubstituted sugar units (x) is between about 20 mol % to about 98 mol %. The mol % of the cationic ether substituted sugar units (y) is preferably about 4 mol % to about 65 mol % and most preferably about 5 mol % to about 50 mol %.

The starch base from which the cationic modified starch is derived can come from various sources such as potato, corn, rice, tapioca or wheat. The preferred starch base from which the cationic modified starch is derived is potato. Further, the weight average molecular weight of said polymer, as determined by gel permeation chromatography (GPC) equipped with refractive index (RI) and multi angle laser light scattering (MALLS) detection units, is at least about 1,000, preferably from about 1,000 to about 10,000,000, more preferably from about 5,000 to about 500,000. Alternatively, dilute solution viscometry can be used to estimate molecular weight. The cationic starch can be prepared by methods known to those skilled in the art, as described, for example, in U.S. Pat. No. 4,127,563.

The aqueous solution of a modified starch according to the present invention the modified starch can be a nonionic modified starch wherein $R^1$ is generally described as: (5) $-CO-(-CHR^8)_m-C\ R^8H_2$; wherein m and $R^8$ are as defined above, the mol % of aliphatic carboxylic acid, substituted sugar units (w) out of the total sugar units along the starch molecule comprises from about 1 mol % to about 50 mol %, preferably from about 4 mol % to about 35 mol % and most preferably from about 5 mol % to about 25 mol %.

The starch base from which the nonionic modified starch is derived can come from various sources such as potato, corn, rice, tapioca or wheat. The preferred starch base from which the nonionic modified starch is derived is potato. Further, the weight average molecular weight of said polymer, as determined by gel permeation chromatography (GPC) equipped with refractive index and multi angle laser light scattering detection units, is at least about 1,000, preferably from about 10,000 to about 10,000,000, more preferably from about 50,000 to about 500,000. Alternatively, dilute solution viscometry can be used to estimate molecular weight. The nonionic starch can be prepared by methods known to those skilled in the art, as described, for example, in U.S. Pat. No. 3,839,320.

The instant invention is also directed to aqueous solutions of the modified starch conditioning additives described. This aqueous solution comprises, on a weight basis, from about 20% to about 98.599%, preferably about 30% to about 80% and most preferably from about 35% to about 75% by weight of water; from about 1% to about 49.5%, preferably about 2% to about 45%, more preferably about 5% to about 40% and most preferably about 10 to about 35% of the above described modified starch; from about 0.2% to about 15%, preferably about 0.5% to about 10% and most preferably about 1% to about 8% of urea;

from about 0.2% to about 10%, preferably about 0.5 to about 8% and most preferably about 1% to about 6% of an alpha hydroxy acid or the corresponding alpha hydroxy acid salt with sodium, ammonium, potassium, and/or any substituted amine, such as diethanolamine, triethanolamine, and monoethanolamine. Any alpha hydroxy acid can be used preferred alpha hydroxy acids are lactic acid, 2-hydroxybutyric acid, 2-hydroxyisobutyric acid, 2-hydroxymethylbutyric acid, 2-hydroxyvaleric acid, with lactic acid being most preferred; from zero to about 5%, preferably 0.1% to about 3%, most preferably 0.5% to about 2% of an aliphatic carboxylic acid from $C_2$ to $C_{36}$ in chain length acid or the corresponding carboxylic acid salt with sodium, ammonium and/or potassium, with acetic acid being most preferred; and from about 0.001% to about 0.5% by weight of a preservative selected from the group consisting of any of the esters of parahydroxybenzoic acid, including ethyl, methyl, propyl, butyl, and isobutyl; benzoic acid and its corresponding sodium, potassium and ammonium salts; chloromethyl isothiazolinone and methyl isothiazolinone; DMDM Hydantoin; imidazolidinyl urea; Quaternium 15; diazolinyl urea; bromo nitro propane diol; formaldehyde; sorbic acid and its corresponding sodium, potassium and ammonium salts; and dibromodicyanobutane.

The pH of the aqueous solutions of the modified starch conditioning additives can be from 1 to 9, with a preferred pH range being from 2 to 8 and the most preferred pH range being from 3 to 7.

The aqueous solutions of the modified starch conditioning additives are unique in that after standing at room temperature for six months the solution does not form a precipitate, become a non pourable gel or separate or spoil due to attack from microorganisms.

More particularly, the instant invention relates to aqueous solutions of the previously described modified starch compositions and methods for treating keratin in which a cosmetically acceptable medium is used which contains at least about 0.01% by weight of the modified starch composition. Preferably, the cosmetically acceptable medium is a hair care product such as a shampoo, conditioner, styling product, rinse or hair coloring composition, or a skin care product such as a cleaner, lotion or cream.

The modified starch and aqueous modified starch conditioning additives for hair care products disclosed herein improve wet and dry hair combability, especially detangling, wet comb and reduced static flyaway, sheen and fixative properties, especially curl retention as well as leaving the hair soft and shiny.

These modified starch conditioning additives are added to hair or skin care product formulations in amounts ranging from about 0.01 to about 20% by weight, based on total formulation weight. They are particularly compatible with anionic surfactant-containing products such as shampoos, generally providing clear formulations without the loss of conditioning properties described above.

The present invention also relates to a method of treating keratin which comprises contacting a keratin-containing substrate with an effective amount of a cosmetically acceptable medium containing from 0.01–20%, by weight, of an instant modified starch.

The instant invention is further directed to a cosmetically acceptable medium containing from about 0.01 to about 20%, based on the total weight of at least said medium, of one of the instant modified starch conditioning additives, wherein said medium is selected, inter alia, from the group consisting of shampoos, aftershaves, sunscreens, hand lotions, liquid soaps, bar soaps, bath oil bars, shaving creams, dishwashing liquids, conditioners, hair dyes, permanent waves, hair relaxers, hair bleaches, hair settings, styling gels, or shower gels. Preferably, the modified starch conditioning additive concentration is from about 0.1 to about 10%, based on total medium weight; most preferably from about 0.2 to about 6%, based on total medium weight.

The instant invention is also directed to a method for treating a keratin-containing substrate comprising: contacting said substrate with an effective amount of a cationic modified starch in which $R^1$ is (2) —$CH_2$—(—$CHR^2$—)$_m$—$CH_2$—$N^+(CH_3)_3 X^-$, wherein m is an integer from 0 to 34, each $R^2$ can independently be H or OH, and $X^-$ is $Cl^-$ or $Br^-$. This starch is preferably of the general formula:

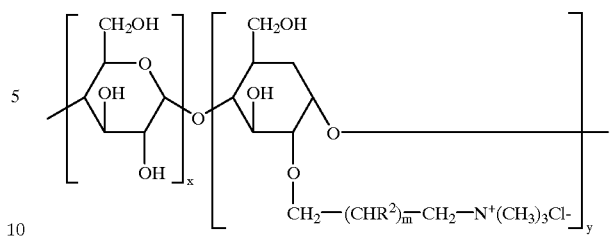

where m is an integer from 0 to 34, $R^2$ can independently be H or OH, and the mol % of the cationic ether substituted sugar units (y) out of the total sugar units along the starch molecule comprises about 2 mol % to about 80 mol % and the mol % of unsubstituted sugar units (x) is between about 20 mol % to about 98 mol %. The mol % of the cationic ether substituted sugar units (y) is preferably about 4 mol % to about 65 mol % and most preferably about 5 mol % to about 50 mol %. Further, the weight average molecular weight of said polymer, as determined by gel permeation chromatography (GPC) equipped with refractive index and multi angle laser light scattering detection units, is at least about 1,000, preferably from about 1,000 to about 10,000,000, more preferably from about 5,000 to about 500,000.

The instant invention is also directed to a method for treating a keratin-containing substrate comprising: contacting said substrate with an effective amount of a modified starch conditioning additive, wherein said additive is described by the structure:

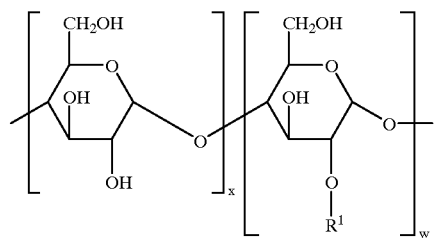

wherein $R^1$, x, and w are as defined above and wherein the mol % of substituted sugar units (w) out of the total sugar units along the starch molecule is between about 2 mol % to about 80 mol % and the mol % of unsubstituted sugar units (x) is between about 20 mol % to about 98 mol %.

The instant invention is also directed to a method for treating a keratin-containing substrate comprising: contacting said substrate with an effective amount of a nonionic modified starch conditioning additive, wherein $R^1$ is generally described as: (5) —CO—(—$CHR^8$—)$_m$—C $R^8H_2$; wherein m and $R^8$ are as defined above, the mol % of aliphatic carboxylic acid, substituted sugar units (w) out of the total sugar units along the starch molecule comprises from about 1 mol % to about 50 mol %, preferably from about 4 mol % to about 35 mol % and most preferably from about 5 mol % to about 25 mol %. Further, the weight average molecular weight of said polymer, as determined by gel permeation chromatography (GPC) equipped with refractive index and multi angle laser light scattering detection units, is at least about 1,000, preferably from about 1,000 to about 10,000,000, more preferably from about 5,000 to about 500,000.

As used herein, the term "keratin" refers to human or animal hair, skin and/or nails.

Further, It will be appreciated that fragile or brittle nails can be strengthened or hardened, and the appearance of the nails improved, as a result of the use of the instant modified starch compositions.

As used herein, the term "active basis" refers to a concentration of additive based on the active solids in the stock solution.

As used herein, the term "effective amount" refers to that amount of a composition necessary to bring about a desired result, such as, for example, the amount needed to treat a keratin-containing substrate relative to a particular purpose, such as conditioning.

As used herein, the term "precipitate" refers to the formation of solid particles in a solution that did not contain such particles when it was initially produced.

As used herein, the term "non pourable gel" refers to a solution that will not pour freely from a container or will move from the container as a single mass. The term "gel" is well known in the art.

As used herein, the term "separate" refers to a solution that was uniform when prepared but subsequently forms two or more distinct layers.

As used herein, the term "spoil" refers to a solution that is able to support the growth of microorganisms such as mold, yeast or bacteria. Solutions in this situation are often characterized by an odor and/or loss of viscosity.

An example of a preferred modified starch is one wherein the mol percentages in the cationic modified starch conditioning additive are 75% unsubstituted sugar (x) and 25% hydroxypropyltrimethyl ammonium chloride ether substituted sugar (y) and a weight average molecular weight as measured by GPC/RI/MALLS of about 150,000 daltons. Another preferred modified starch composition is one wherein the mol percentages in the nonionic modified starch conditioning additive are 90% unsubstituted sugar (x) and 10% acetic acid substituted sugar (w) with a weight average molecular weight as measured by GPC/RI/MALLS of about 200,000 daltons. The modified starch conditioning additives are added to a cosmetically acceptable medium at a concentration of from about 0.1 to about 10%, by weight, based on total medium weight. Methods of adding the modified starch conditioning additives to a cosmetically acceptable medium are well known to those familiar with the art. The preferred mode also entails use of an effective amount of the modified starch conditioning additive containing medium in the treatment of a keratin-containing substrate, preferably human skin or hair. Methods of using such compositions are well known in the art.

The modified starch conditioning additives of the present invention are used in compositions for treating hair, skin or nails by incorporating them in a cosmetically acceptable medium used to treat hair, skin or nails in amounts of about 0.01 to about 20%, on an active polymer basis, based on the total weight of said medium, and preferably in an amount of from about 0.1 to about 10% active polymer based on total medium weight.

These compositions can be presented in various forms, i.e., various cosmetically acceptable media, such as a liquid, cream, emulsion, gel, thickening lotion or powder; they can contain water and also any cosmetically acceptable solvent, in particular monoalcohols, such as alkanols having 1 to 8 carbon atoms (like ethanol, isopropanol, benzyl alcohol and phenylethyl alcohol) polyalcohols, such as alkylene glycols (like glycerine, ethylene glycol and propylene glycol) and glycol ethers, such as mono-, di- and tri-ethylene glycol monoalkyl ethers, for example ethylene glycol monomethyl ether and diethylene glycol monomethyl ether, used singly or in a mixture. These solvents can be present in proportions of up to as much as 70% by weight, relative to the weight of the total composition.

The surface of pigments, such titanium dioxide, zinc oxide, talc, calcium carbonate or kaolin, can be treated with the modified starches of this invention. The treated pigments are then more effective as sunscreen actives and for use in color cosmetics such as make up and mascara.

These compositions can also be packaged as an aerosol, in which case they can be applied either in the form of an aerosol spray or in the form of an aerosol foam.

As the propellant gas for these aerosols, it is possible to use, in particular, dimethyl ether, carbon dioxide, nitrogen, nitrous oxide, air and volatile hydrocarbons, such as butane, isobutane, propane and, possibly, chlorinated and fluorinated hydrocarbons, although the latter are falling into increasing environmental disfavor.

Preferred compositions can also contain electrolytes, such as aluminum chlorohydrate, alkali metal salts, e.g., sodium, potassium or lithium salts, these salts preferably being halides, such as the chloride or bromide, and the sulfate, or salts with organic acids, such as the acetates or lactates, and also alkaline earth metal salts, preferably the carbonates, silicates, nitrates, acetates, gluconates, pantothenates and lactates of calcium, magnesium and strontium.

These compositions can also be presented in the form of a powder or of lyophilisates to be diluted before use.

The compositions according to the present invention can contain any other ingredient normally used in cosmetics, such as perfumes, dyestuffs which can serve to color the composition itself or hair fibers, preservatives, sequestering agents, thickeners, silicones, softeners, foam synergistic agents, foam stabilizers, sun filters, peptizing agents and also anionic, non-ionic, cationic or amphoteric surface-active agents or mixtures thereof.

These compositions can be used, in particular, in the form of a shampoo, a rinsing lotion, a cream or a treatment product which can be applied before or after coloring or bleaching, before or after shampooing, before or after perming or before or after straightening, and can also adopt the form of a coloring product, a setting lotion, a brushing lotion, a bleaching product, a perming product or a straightening product.

A particularly preferred embodiment consists of use in the form of a shampoo for washing the hair.

In this case, these compositions contain anionic, cationic, nonionic and/or amphoteric surface-active agents typically in an amount from 3–50% by weight, preferably 3–20%, and their pH is general in the range of 3 to 10.

A list of the surface-active agents which can be used according to the invention is given U.S. Pat. Nos. 4,240,450; 4,445,521 and 4,719,099. The disclosures of which are incorporated in their entirety by reference.

The shampoo for washing hair can also contain other conditioning additives such as silicones and conditioning polymers typically used in shampoos. U.S. Pat. No. 5,573,709 provides a list of non volatile silicone conditioning agents that can be used in shampoos. The disclosure of which is incorporated in its entirety by reference. The conditioning polymers that can be used are listed in the Cosmetic, Toiletries and Fragrance Associations (CTFA) dictionary and include the Polyquaterniums (example Polyquaternium-1 to Polyquaternium-47), Guar Hydroxypropyl Trimonium Chloride and Polymethacrylamidopropyl Trimonium Chloride.

Other preferred embodiments consist of use in the form of a rinsing lotion to be applied mainly before or after shampooing. These lotions are typically aqueous or aqueous-alcoholic solutions, emulsions, thickened lotions or gels. If the compositions are presented in the form of an emulsion, they can be nonionic, anionic or cationic. The nonionic emulsions consist mainly of a mixture of an oil and/or a fatty alcohol with a polyoxyethyleneated alcohol, such as polyoxyethyleneated stearyl or cetyl/stearyl alcohol, and cationic surface-active agents can be added to these compositions. The anionic emulsions are formed essentially from soap.

If the compositions are presented in the form of a thickened lotion or a gel, they contain thickeners in the presence or absence of a solvent. The thickeners which can be used are especially carbopol, xanthan gums, sodium alginates, gum arabic, cellulose derivatives and poly(ethylene oxide) based thickeners, and it is also possible to achieve thickening by means of a mixture of polyethylene glycol stearate or distearate or by means of a mixture of a phosphoric acid ester and an amide. The concentration of thickener is generally 0.05 to 15% by weight. If the compositions are presented in the form of a styling lotion, shaping lotion, or setting lotion, they generally comprise, in aqueous, alcoholic or aqueous-alcoholic solution, the modified starches defined above.

If the compositions of the instant invention are intended for use in the dyeing of keratin fibers, and in particular human hair, they generally contain at least one oxidation dyestuff precursor and/or one direct dyestuff, in addition to the modified starches. They can also contain any other adjuvant normally used in this type of composition.

The pH of the dyeing compositions is generally 7 to 11 and can be adjusted to the desired value by adding an alkalizing agent.

The compositions according to the present invention can also be used for waving or straightening the hair. In this case, the composition generally contains, in addition to the modified starch composition, one or more reducing agents and, if appropriate, other adjuvants normally used in this type of composition; such compositions are intended for use conjointly with a neutralizing composition.

EXAMPLES

The following examples illustrate the intended use of the instant invention. They are not intended, however, to limit these inventions in any way.

Examples 1–4

Test Shampoo Formulations:

The ingredients are added to a beaker equipped with an overhead stirrer in the order listed in the table below at room temperature.

TABLE 1

| SHAMPOO | | | | | |
|---|---|---|---|---|---|
| INGREDIENTS | INCI NAME | 1 | 2 | 3 | 4 |
| Standapol A | Ammonium lauryl sulfate | 7.50 | 7.50 | 7.50 | 7.50 |
| Standapol EA-3 | Ammonium laureth sulfate | 17.50 | 17.50 | 17.50 | 17.50 |
| Tegobetaine L-7 | Cocamidopropyl betaine | 5.0 | 5.0 | 5.0 | 5.0 |
| Monamid 1113 | Cocamide DEA | 3.0 | 3.0 | 3.0 | 3.0 |
| Solance ®[1] | Modified Starch | | 0.26 | | |
| Cationic modified starch[2] | | | | 0.26 | |
| Nonionic modified starch[3] | | | | | 0.26 |
| Tween 20 | Polysorbate 20 | 1.00 | 1.00 | 1.00 | 1.00 |
| Sodium Chloride | Sodium Chloride | 0.75 | 0.75 | 0.75 | 0.75 |
| Glydant | DMDM hydantoin | 0.20 | 0.20 | 0.20 | 0.20 |

TABLE 1-continued

| SHAMPOO | | | | | |
|---|---|---|---|---|---|
| INGREDIENTS | INCI NAME | 1 | 2 | 3 | 4 |
| Citric Acid | Citric Acid | q.s. to pH 6 | q.s. to pH 6 | q.s. to pH 6 | q.s. to pH 6 |
| Water, D.I. | Water | q.s. to 100 | q.s. to 100 | q.s. to 100 | q.s. to 100 | q.s. refers to quantity sufficient
[1]amphoteric modified starch from National Starch described in U.S. Pat. No. 5,871,756
[2]cationic modified starch conditioning additive with 75% unsubstituted sugar (x) and 25% hydroxypropyltrimethyl ammonium chloride substituted sugar (Y) and Mw of about 150,000 daltons.
[3]nonionic modified starch conditioning additive with 90% unsubstituted sugar (x) and 10% acetic acid ester substituted sugar (Z) and Mw of about 200,000 daltons. all ingredients added on an active weight percentage basis.

The formulas remained uniform after one month at room temperature.

TESTS:

The test shampoo formulations above were evaluated for wet combing vs. a control with no conditioning additive (Example 1) and a less preferred control with a corresponding amount of a commercially available amphoteric starch (Example 2). Results are shown in Table 1 below.

TABLE 2

| Example # | Wet Comb (mJoules) |
|---|---|
| 1 Control - no polymer | 219 |
| 2 Solance ® | 92 |
| 3 Cationic modified starch | 67 |
| 4 Nonionic modified starch | 71 |

Good hair conditioning is indicated when less work (mJoules) are required to comb the hair tress. The examples demonstrate the conditioning benefit of the modified starches of the current invention on hair.

Examples 5–8

Hydro Lotion Formulations:

The Hydro Lotion outlined below is meant to prevent dry skin by providing increased skin moisture content. The following Hydro Lotion variations were prepared in a beaker equipped with a heating element, thermometer and overhead stirrer, water was added and heated to 70° C. The acrylates/vinyl isodecanoate crosspolymer was added and mixed until uniform. Triethanolamine, glycerine and modified starch solution (if called for) were then added and mixed until uniform. In a separate beaker, equipped as the first, caprylic/capric triglyceride, octyldodecanol and cetearyl alcohol were mixed and heated to 70° C. The contents of the second beaker were then added to the first and mixed for 15 minutes. The mixture was then cooled to less than 40° C. and the methyldibromoglutaronitrile and dipropylene glycol, DMDM hydantoin and fragrance were added

TABLE 3

| Ingredient | Example 5 | Example 6 | Example 7 | Example 8 |
|---|---|---|---|---|
| Acrylates/Vinyl Isodecanoate Crosspolymer | 0.30% | 0.30% | 0.30% | 0.30% |
| Water | 89.62% | 89.37% | 89.37% | 89.37% |
| Triethanolamine | 0.18% | 0.18% | 0.18% | 0.18% |
| Glycerine | 3.00% | 3.00% | 3.00% | 3.00% |
| Cationic modified Starch[1] | | 0.25% | | |
| Cationic modified Starch[2] | | | 0.25% | |
| Nonionic modified Starch[3] | | | | 0.25% |
| Caprylic/Capric Triglyceride | 3.00% | 3.00% | 3.00% | 3.00% |
| Octyldodecanol | 2.00% | 2.00% | 2.00% | 2.00% |
| Cetearyl Alcohol | 1.50% | 1.50% | 1.50% | 1.50% |
| 5% Dibromo-dicyanobutane in dipropylene glycol | 0.10% | 0.10% | 0.10% | 0.10% |
| DMDM Hydantoin | 0.10% | 0.10% | 0.10% | 0.10% |
| Fragrance | 0.20% | 0.20% | 0.20% | 0.20% |

[1]cationic modified starch conditioning additive with 50% unsubstituted sugar (X) and 50% hydroxypropyltrimethyl ammonium chloride substituted sugar (Y) and Mw of about 150,000 daltons.
[2]cationic modified starch conditioning additive with 85% unsubstituted sugar (X) and 15% hydroxypropyltrimethyl ammonium chloride substituted sugar (Y) and Mw of about 200,000 daltons.
[3]nonionic modified starch conditioning additive with 90% unsubstituted sugar (X) and 10% acetic acid ester substituted sugar (Z) and Mw of about 200,000 daltons.

The formulas remained uniform after one month at room temperature.

Tests:

These examples demonstrate the ability of the modified starch compositions of the invention to condition skin.

A 50 year old female panelist pre-washed the volar surfaces of both of her forearms with Ivory® soap, for five days prior to testing. The NOVA™ DPM 9003 (Dermal Phase Meter) with standard DPM 9103 (8.76 mm) sensor probe was used to measure moisturization. The panelist was equilibrated for 30 minutes in an environmental chamber at 22° C. and 50% RH prior to taking any measurements. Baseline skin readings were taken at each of the test sites. The application dosage was 0.05 g/6.25 cm2. Measurements were taken at 15, 30, 60, 90 and 120 minutes after application. The reported value is mean delta, the difference between the average of the triplicate measurements from treated skin and the baseline untreated skin measurement.

TABLE 4

| Time (min.) | Example 5 | Example 6 | Example 7 | Example 8 |
|---|---|---|---|---|
| 15 | 37 | 58 | 53 | 58 |
| 30 | 38 | 58 | 53 | 60 |
| 60 | 29 | 45 | 41 | 52 |
| 90 | 31 | 51 | 55 | 49 |
| 120 | 33 | 52 | 54 | 51 |

The data demonstrate the skin moisturizing benefit derived from the modified starch conditioning additives, as demonstrated by the higher moisture content of the skin (i.e., higher mean delta) over time.

What is claimed:

1. An aqueous solution of a modified starch comprising:
   (a) about 20% to about 98.599%, by weight water;
   (b) about 1% to about 49.5%, by weight of a modified starch;
   (c) about 0.2% to about 15%, by weight of urea;
   (d) about 0.2% to about 10% by weight of an alpha hydroxy acid or the corresponding alpha hydroxy acid salt with sodium, ammonium, potassium, and/or substituted amine;
   (e) zero up to about 5% by weight of an aliphatic carboxylic acid from $C_2$ to $C_{36}$ in chain length acid or the corresponding carboxylic acid salt with sodium, ammonium and/or potassium;
   (f) about 0.001% to about 0.5% by weight of a preservative; and
   (g) having a pH of from about 1 to 9 wherein the modified starch of (b) is of the general formula:

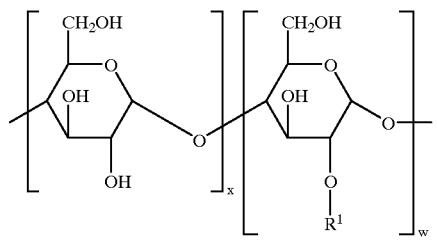

wherein $R^1$ is selected from the group consisting of ethers (1,2,3 and 4), ester (5) and amphoteric stubstituents (6, 7, 8 and 9) generally described as:

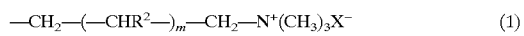

wherein m is an integer from 0 to 34, each $R^2$ can independently be H or OH, and $X^-$ is $Cl^-$ or $Br^-$;

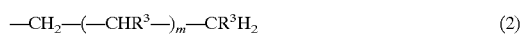

wherein m is as defined above and each $R^3$ can independently be H or OH;

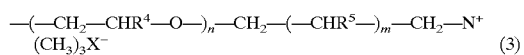

wherein n is an integer from 1 to 100, m is as defined above, each $R^4$ can independently be H, OH, $CH_3$ or $CH_2OH$, each $R^5$ can independently be H or OH, and $X^-$ is $Cl^-$ or $Br^-$;

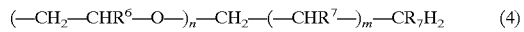

wherein n and m are as defined above, each $R^6$ can independently be H, OH, $CH_3$ or $CH_2OH$, each $R^7$ can independently be H or OH, and $X^-$ is $Cl^-$ or $Br^-$;

wherein m is as defined above and each $R^8$ can independently be H, OH, $CH_3$ or $CH_2OH$;

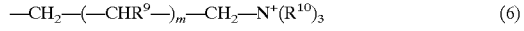

wherein m is as defined above, each $R^9$ can independently be H, OH, $CH_3$ or $CH_2OH$, and each $R_{10}$ can independently be:

(A) 

(B) 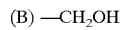

(C) 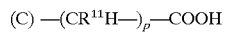

(D) —(CR¹¹H—)$_p$—COO⁻

(E) —(CR¹¹H—)$_p$—SO$_3^-$ wherein p is an integer from zero to 10 and each R¹¹ can independently be H, OH, CH$_3$ or CH$_2$OH;

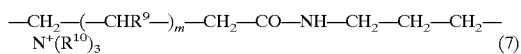  (7)

wherein m, R⁹, and R¹⁰ are as defined above;

—CO—CH$_2$—(—CHR⁹—)$_m$—CH$_2$—N⁺(R¹⁰)$_3$  (8)

wherein m, R⁹, and R¹⁰ are as defined above;

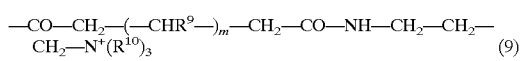  (9)

wherein m, R⁹ and R¹⁰ are as defined above;
wherein the mol % of substituted sugar units (w) out of the total sugar units along the starch molecule is between about 2 mol % to about 80 mol % and the mol % of unsubstituted sugar units (x) is between about 20 mol % to about 98 mol %.

2. The aqueous solution of a modified starch according to claim 1 wherein the modified starch is of the general formula:

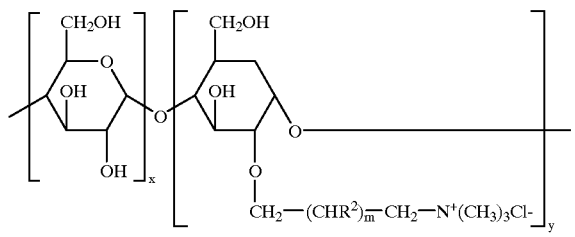

wherein m is as defined above, the mol % of cationic ether substituted sugar units (y) out of the total sugar units along the starch molecule is between about 2 mol % to about 80 mol %, and the mol % of unsubstituted sugar units (x) is between about 20 mol % to about 98 mol %.

3. The aqueous solution of a modified starch according to claim 1 wherein the modified starch is a nonionic starch wherein R¹ is generally described as:

—CO—(—CHR⁸)$_m$—C R⁸H$_2$  (5)

wherein m and R⁸ are as defined in claim 1, the mol % of aliphatic carboxylic acid ester, substituted sugar units (w) out of the total sugar units along the starch molecule comprises from about 1 mol % to about 50 mol %.

4. The aqueous solution of a modified starch according to claim 1 wherein the preservative (f) is selected from the group consisting of the methyl, ethyl, propyl, butyl, and isobutyl esters of parahydroxybenzoic acid; benzoic acid and its corresponding sodium, potassium and ammonium salts; chloromethyl isothiazolinone and methyl isothiazolinone; DMDM Hydantoin; imidazolidinyl urea; Quaternium 15; diazolinyl urea; bromo nitro propane diol; formaldehyde; sorbic acid and its corresponding sodium, potassium and ammonium salts; and dibromodicyanobutane.

5. The aqueous solution of a modified starch according to claim 1 wherein the alpha hydroxy acid (d) or corresponding salt is selected from the group consisting of lactic acid, 2-hydroxybutyric acid, 2-hydroxyisobutyric acid, 2-hydroxymethylbutyric acid, and 2-hydroxyvaleric acid.

6. The aqueous solution of a modified starch according to claim 5 wherein the alpha hydroxy acid (d) is lactic acid.

7. The aqueous solution of a modified starch according to claim 3 wherein the aliphatic carboxylic acid (e) is present in a concentration of about 0.1 to about 3% by weight and is acetic acid.

8. The aqueous solution of a modified starch according to claim 1 wherein the modified starch (b) is present in a concentration of about 5% to about 40% by weight.

9. The aqueous solution of a modified starch according to claim 1 wherein the modified starch has a (number or weight) average molecular weight of about 5,000 to about 500,000.

10. A cosmetically acceptable medium comprising about 0.1 to about 20%, based on the weight of said medium, of the aqueous solution of the modified starch of claim 1.

11. A cosmetically acceptable medium comprising about 0.1 to about 20%, based on the weight of said medium, of the aqueous solution of the modified starch of claim 2.

12. A cosmetically acceptable medium comprising about 0.1 to about 20%, based on the weight of said medium, of the aqueous solution of the modified starch of claim 3.

13. A method for treating a keratin-containing substrate comprising contacting said substrate with an effective amount of a cosmetically acceptable medium comprising from about 0.1 to about 20% by weight of the aqueous solution of the modified starch of claim 1.

14. A method for treating a keratin-containing substrate comprising contacting said substrate with an effective amount of a cosmetically acceptable medium comprising from about 0.1 to about 20% by weight of the aqueous solution of the modified cationic starch of claim 2.

15. A method for treating a keratin-containing substrate comprising contacting said substrate with an effective amount of a cosmetically acceptable medium comprising from about 0.1 to about 20% by weight of the aqueous solution of the modified nonionic starch of claim 3.

16. The method according to claim 13 wherein said cosmetically acceptable medium is selected from the group consisting of a shampoo, an aftershave, a sunscreen, a hand lotion, a liquid soap, a bar soap, a bath oil bar, a shaving cream, a dishwashing liquid, a conditioner, a hair dye, a permanent wave, a hair relaxer, a hair bleach, a hair setting formulation, a styling gel, and a shower gel.

17. The method according claim 14 wherein said cosmetically acceptable medium is selected from the group consisting of a shampoo, an aftershave, a sunscreen, a hand lotion, a liquid soap, a bar soap, a bath oil bar, a shaving cream, a dishwashing liquid, a conditioner, a hair dye, a permanent wave, a hair relaxer, a hair bleach, a hair setting formulation, a styling gel, and a shower gel.

18. The method according to claim 15 wherein said cosmetically acceptable medium is selected from the group consisting of a shampoo, an aftershave, a sunscreen, a hand lotion, a liquid soap, a bar soap, a bath oil bar, a shaving cream, a dishwashing liquid, a conditioner, a hair dye, a permanent wave, a hair relaxer, a hair bleach, a hair setting formulation, a styling gel, and a shower gel.

* * * * *